US006183761B1

(12) United States Patent
Bissett et al.

(10) Patent No.: US 6,183,761 B1
(45) Date of Patent: Feb. 6, 2001

(54) COMPOSITIONS FOR REGULATING SKIN APPEARANCE

(75) Inventors: Donald Lynn Bissett, Hamilton; John Erich Oblong, Loveland, both of OH (US)

(73) Assignee: The Procter & Gamble Company, Cincinnati, OH (US)

( * ) Notice: Under 35 U.S.C. 154(b), the term of this patent shall be extended for 0 days.

(21) Appl. No.: 09/267,852

(22) Filed: Mar. 12, 1999

Related U.S. Application Data

(60) Provisional application No. 60/078,158, filed on Mar. 16, 1998.

(51) Int. Cl.[7] ................ A61K 6/00; A61K 7/00; A61K 47/32

(52) U.S. Cl. .......... 424/401; 514/844; 514/846; 514/847; 514/848; 424/45; 424/47; 424/59; 424/60; 424/70.1; 424/70.11

(58) Field of Search .............. 424/401, 45, 47, 424/70.1, 70.11, 60, 59; 514/772.6, 844, 846, 847, 848

(56) References Cited

U.S. PATENT DOCUMENTS

| | | | |
|---|---|---|---|
| 4,190,671 | 2/1980 | Vanstone et al. | 424/317 |
| 4,219,569 | 8/1980 | Glenn | 424/331 |
| 4,279,930 | 7/1981 | Hall et al. | 424/331 |
| 4,439,418 | 3/1984 | Möller et al. | 424/70 |
| 4,584,190 | 4/1986 | Tejima et al. | 424/59 |
| 4,699,924 | 10/1987 | Durrant et al. | 514/558 |
| 4,758,599 | 7/1988 | Minetti | 514/844 |
| 4,834,076 | 5/1989 | Millet et al. | 128/65 |
| 4,867,964 | 9/1989 | Forestier et al. | 424/47 |
| 4,938,960 | 7/1990 | Ismail | 424/195.1 |
| 5,043,356 | 8/1991 | Fulton, Jr. | 514/549 |
| 5,179,091 | 1/1993 | Lesieur et al. | 514/224.5 |
| 5,254,331 | 10/1993 | Mausner | 424/59 |
| 5,276,058 | 1/1994 | Satoh et al. | 514/646 |
| 5,362,494 | 11/1994 | Zysman et al. | 424/401 |
| 5,443,840 | 8/1995 | Morancais et al. | 424/450 |
| 5,519,039 | 5/1996 | Leung | 514/356 |
| 5,520,919 | 5/1996 | Lerner | 424/401 |
| 5,539,129 | 7/1996 | Zysman et al. | 549/430 |
| 5,541,220 | 7/1996 | Ismail | 514/458 |
| 5,545,399 | 8/1996 | Lee et al. | 424/59 |
| 5,556,887 | 9/1996 | Lerner | 514/772.6 |
| 5,626,868 | 5/1997 | Morancais et al. | 424/450 |
| 5,833,998 | 11/1998 | Biedermann et al. | 424/401 |
| 6,093,411 | * 7/2000 | Bissett | 424/401 |

FOREIGN PATENT DOCUMENTS

| | | | |
|---|---|---|---|
| 2242553 | 3/1974 | (DE) | A61K/7/00 |
| 052705 A1 | 6/1982 | (EP) | A61K/31/455 |
| 512814 A1 | 11/1992 | (EP) | A61K/7/48 |
| 811595 A1 | 12/1997 | (EP) | C07C/39/15 |
| 2580478 | 4/1985 | (FR) | A45D/24/22 |
| 2669225 | 5/1992 | (FR) | A61K/35/78 |
| 2694692 | 2/1994 | (FR) | A61K/7/48 |
| 2695561 A1 | 3/1994 | (FR) | A61K/31/705 |
| 60-81014 | 9/1985 | (JP) | A61K/7/50 |
| 63-096120 | 4/1988 | (JP) | A61K/7/42 |
| 63-135309 | 6/1988 | (JP) | A61K/7/00 |
| 04305512 | 10/1992 | (JP) | A61K/7/00 |
| 05213729 | 8/1993 | (JP) | A61K/7/42 |
| 05246932 | 9/1993 | (JP) | C07C/49/835 |
| 05255655 | 10/1993 | (JP) | C09K/3/00 |
| 06321764 | 11/1994 | (JP) | A61K/7/48 |
| 08012522 | 1/1996 | (JP) | A61K/7/00 |
| 08113521 | 5/1996 | (JP) | A61K/7/42 |
| 08217622 | 8/1996 | (JP) | A61K/7/00 |
| 08217623 | 8/1996 | (JP) | A61K/7/00 |
| 09002952 | 1/1997 | (JP) | A61K/31/455 |
| 09143087 | 6/1997 | (JP) | A61K/35/78 |
| 09194383 | 7/1997 | (JP) | A61K/35/72 |
| 10101543 | 4/1998 | (JP) | A61K/7/48 |
| 10330259 A2 | 12/1998 | (JP) | A61K/31/35 |
| 9202206 | 2/1992 | (WO) | A61K/7/48 |
| 9205137 | 4/1992 | (WO) | C07C/49/835 |
| 9407462 | 4/1994 | (WO) | A61K/7/48 |
| 9409756 | 5/1994 | (WO) | A61K/7/48 |
| 9511662 | 5/1995 | (WO) | A61K/7/42 |
| 9625943 | 8/1996 | (WO) | A61K/38/28 |
| 9637420 | 11/1996 | (WO) | B65D/81/32 |
| 9701345 | 1/1997 | (WO) | A61K/35/78 |
| 9701346 | 1/1997 | (WO) | A61K/35/78 |
| 9706659 A2 | 2/1997 | (WO) | . |
| 9718804 | 5/1997 | (WO) | A61K/31/19 |
| 9739733 | 10/1997 | (WO) | A61K/7/48 |
| 9822084 A1 | 5/1998 | (WO) | A61K/7/48 |
| 9852927 A1 | 11/1998 | (WO) | C07D/241/36 |
| 9204116 | 2/1993 | (ZA) | . |

OTHER PUBLICATIONS

ASCS Conference presentation, "Effects of Niacinamide on Ceramide Biosynthesis and Differentiation of Cultured Human Keratinocytes" (Kanebo).

* cited by examiner

*Primary Examiner*—Thurman K. Page
*Assistant Examiner*—S. Howard
(74) *Attorney, Agent, or Firm*—Darryl C. Little; Armina E. Matthews

(57) ABSTRACT

The present invention relates to compositions for preventing or treating skin disorders using vitamin B3 compounds and polycyclic compounds. The present invention also relates to methods for regulating skin condition.

10 Claims, No Drawings

COMPOSITIONS FOR REGULATING SKIN APPEARANCE

CROSS REFERENCE

This application claims priority under Title 35, United States Code 119(e) from Provisional application Ser. No. 60/078,158, filed Mar. 16, 1998

TECHNICAL FIELD

The present invention relates to composition for preventing or treating skin disorders using vitamin B3 compounds and polycyclic compounds. The present invention also relates to methods for regulating skin condition.

BACKGROUND OF THE INVENTION

Many personal care products currently available to consumers are directed primarily to improving the health and/or physical appearance of the skin. Among these skin care products, many are directed to delaying, minimizing or even eliminating skin wrinkling and other histological changes typically associated with the aging of skin or environmental damage to human skin. Other types of products are useful for imparting moisturization to dry skin, providing photoprotection for skin exposed to sunlight, and bringing about desired control of pigmentation, especially lightening of darkened or hyperpigmented skin.

Skin is subject to insults by many extrinsic and intrinsic factors. Extrinsic factors include ultraviolet radiation (e.g., from sun exposure), environmental pollution, wind, heat or infrared radiation (IR), low humidity, harsh surfactants, abrasives, and the like. Intrinsic factors include chronological again and other biochemical changes from within the skin. Whether extrinsic or intrinsic, these factors result in visible signs of skin aging and environmental damage, such as wrinkling and other forms of roughness (including increased pore size, flaking and skin lines), and other histological changes associated with skin aging or damage. To many people, skin wrinkles are a reminder of the disappearance of youth. As a result, the elimination of wrinkles has become a booming business in youth-conscious societies. Treatments range from cosmetic creams and moisturizers to various forms of cosmetic surgery.

Extrinsic or intrinsic factors may result in the thinning and general degradation of the skin. For example, as the skin naturally ages, there is a reduction in the cells and blood vessels that supply the skin. There is also a flattening of the dermal-epidermal junction which results in weaker mechanical resistance of this junction. See, for example, Oikarinen, "The Aging of Skin: Chronoaging Versus Photoaging," *Photodermatol. Photoimmunol. Photomed.*, vol. 7, pp. 3–4, 1990, which is incorporated by reference herein in its entirety.

It has now been found that topical compositions containing a vitamin $B_3$ compound and select polycyclic compounds provide benefits in regulating skin condition previously unrecognized in the art of which the present inventors are aware. For example, such compositions regulate the signs of skin aging, especially visible and/or tactile discontinuities in skin texture associated with aged skin, including fine lines and wrinkles.

It is therefore an object of the present invention to provide topical compositions for prophylactically and/or therapeutically regulating mammalian skin condition (especially of human skin, more especially facial skin), containing a vitamin $B_3$ compound and a polycyclic compound.

It is another object of the present invention to provide topical compositions for prophylactically and/or therapeutically regulating signs of mammalian skin aging containing a vitamin $B_3$ compound and a polycyclic compound.

It is another object of the present invention to provide topical compositions for prophylactically and/or therapeutically regulating visible and/or tactile discontinuities in mammalian skin texture, including fine lines, wrinkles, enlarged pores, roughness, dryness and other skin texture discontinuities associated with aged skin, containing a vitamin $B_3$ compound and a polycyclic compound.

The present invention also relates to methods of providing such regulation using the subject compositions.

These and other objects of this invention will become apparent in light of the following disclosure.

SUMMARY OF THE INVENTION

The present invention relates to topical compositions comprising:

(a) a safe and effective amount of a vitamin B3 compound;

(b) a safe and effective amount of a polycyclic compound selected from the group consisting of:
  (i) flavanones selected from the group consisting of unsubstituted flavanones, mono-substituted flavanones, and mixtures thereof;
  (ii) chalcones selected from the group consisting of unsubstituted chalcones, mono-substituted chalcones, di-substituted chalcones, tri-substituted chalcones, and mixtures thereof;
  (iii) flavones selected from the group consisting of unsubstituted flavones, mono-substituted flavones, di-substituted flavones, and mixtures thereof;
  (iv) one or more isoflavones;
  (v) coumarins selected form the group consisting of unsubstituted coumarins, mono-substituted coumarins, di-substituted coumarins, and mixtures thereof;
  (vi) chromones selected from the group consisting of unsubstituted chromones, mono-substituted chromones, di-substituted chromones, and mixtures thereof;
  (vii) one or more dicoumarols;
  (viii) one or more chromanones;
  (ix) one or more chromanols; and
  (x) sterols selected from the group consisting of stigmasterol, stigmastanol, brassicasterol, campesterol, and mixtures thereof;
  (xi) triterpenoids selected from the group consisting of betulinic acid, boswellic acid, and mixtures thereof; and
  (x) mixtures thereof;
and (c) a dermatologically acceptable carrier for the vitamin B3 compound and the polycyclic compound.

The present invention further relates to methods for treating and regulating skin condition using the topical compositions.

DETAILED DESCRIPTION OF THE INVENTION

All percentages and ratios used herein are by weight of the total composition and all measurements made are at 25° C., unless otherwise designated.

The compositions of the present invention can comprise, consist essentially of, or consist of, the essential as well as optional ingredients and components described herein. As used herein, "consisting essentially of" means that the composition or component may include additional ingredients, but only if the additional ingredients do not materially alter the basic and novel characteristics of the claimed compositions or methods.

All publications cited herein are hereby incorporated by reference in their entirety.

The term "topical application", as used herein, means to apply or spread the compositions of the present invention onto the surface of the skin.

The term "dermatologically-acceptable," as used herein, means that the compositions or components thereof so described are suitable for use in contact with human skin without undue toxicity, incompatibility, instability, allergic response, and the like.

The term "safe and effective amount" as used herein means an amount of a compound or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound judgment of the skilled artisan.

The compositions of the present invention are useful for topical application and for regulating skin condition, including visible and/or tactile discontinuities in skin (especially the skin surface; such discontinuities are generally undesired). Such discontinuities may be induced or caused by internal and/or external factors, and include the signs of skin aging described herein. "Regulating skin condition" includes prophylactically regulating and/or therapeutically regulating skin condition, including visible and/or tactile discontinuities in skin such as, but not limited to, regulating visible and/or tactile discontinuities in the texture of skin, reducing post-inflammatory hyperpigmentation, regulating non-melanin discoloration of skin, regulating moisturization and barrier properties of skin, regulating epidermal differentiation of skin, regulating exfoliation of skin, thickening of skin to reduce skin atrophy, regulating the elasticity of skin, reducing oily skin, regulating cellulite in skin, regulating pruritus in skin, promoting wound healing in skin, protecting skin from environmental insult, and regulating skin inflammation. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, discontinuities in skin. Regulating skin condition involves improving skin appearance and/or feel.

The compositions of the present invention are useful for regulating signs of skin aging, more especially visible and/or tactile discontinuities in skin texture associated with aging. "Regulating the signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign). As used herein, prophylactically regulating such signs includes delaying, minimizing and/or preventing signs of skin aging. As used herein, therapeutically regulating such signs includes ameliorating, e.g., diminishing, minimizing and/or effacing signs of skin aging.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental insult (e.g., sunlight, UV, smoke, ozone, pollutants, stress, etc.). These signs may result from processes which include, but are not limited to, the development of textural discontinuities such as wrinkles, including both fine superficial wrinkles and coarse deep wrinkles, skin lines, facial frown lines, expression lines, rhytides, dermatoheliosis, photodamage, premature skin aging, crevices, bumps, pits, large pores (e.g., associated with adnexal structures such as sweat gland ducts, sebaceous glands, or hair follicles), "orange'peel" skin appearance, dryness, scaliness, flakiness and/or other forms of skin unevenness or roughness; blemishes such as acne, pimples, breakouts; excess skin oil problems such as over production of sebum, oiliness, facial shine, foundation breakthrough; abnormal desquamation (or exfoliation) or abnormal epidermal differentiation (e.g., abnormal skin turnover) such as scaliness, flakiness, keratoses, hyperkeratinization; inadequate skin moisturization (or hydration) such as caused by skin barrier damage, environmental dryness; loss of skin elasticity (loss and/or inactivation of functional skin elastin) such as elastosis, sagging (including puffiness in the eye area and jowls), loss of skin firmness, loss of skin tightness, loss of skin recoil from deformation;, non-melanin skin discoloration such as(including undereye circles), blotching (e.g., uneven pigmentation or red coloration due to, e.g., rosacea), sallowness (pale color), discoloration caused by telangiectasia or spider vessels; melanin-related hyperpigmented (or unevenly pigmented) skin regions such as age spots (liver spots, brown spots) and freckles; post-inflammatory hyperpigmentation such as that which occurs following an inflammatory event (e.g., as an acne lesion, in-grown hair, insect/spider bite or sting, scratch, cut, wound, abrasion, and the like); and atrophy such as, but not limited to, that associated with aging or steroid use; other histological or microscopic alterations in skin components such as ground substance (e.g., hyaluronic acid, glycosaminoglycans, etc.), collagen breakdown and structural alterations or abnormalities (e.g., changes in the stratum corneum, dermis, epidermis, the skin vascular system such as telangiectasia or spider vessels); tissue responses to insult such as itch or pruritus; and alterations to underlying tissues (e.g., subcutaneous fat, cellulite, muscles, trabeculae, septae, and the like), especially those proximate to the skin.

It is to be understood that the present invention is not to be limited to regulation of the above mentioned "signs of skin aging" which arise due to mechanisms associated with skin aging, but is intended to include regulation of said signs irrespective of the mechanism of origin. As used herein, "regulating skin condition" is intended to include regulation of such signs irrespective of the mechanism of origin.

The present invention is especially useful for therapeutically regulating visible and/or tactile discontinuities in mammalian skin texture, including texture discontinuities associated with skin aging. As used herein, therapeutically regulating such discontinuities includes ameliorating, e.g., diminishing, minimizing and/or effacing visible and/or tactile discontinuities in the texture of mammalian skin, to thereby provide improved skin appearance and/or feel, e.g., a smoother, more even appearance and/or feel. Such visible and/or tactile discontinuities in skin texture include crevices, bumps, pores, fine lines, wrinkles, scales, flakes and/or other forms of textural unevenness or roughness associated with skin aging. For example, the length, depth, and/or other dimension of lines and/or wrinkles are decreased, the apparent diameter of pores decreases, or the apparent height of tissue immediately proximate to pore openings approaches that of the interadnexal skin.

The present invention is also especially useful for prophylactically regulating visible and/or tactile discontinuities in mammalian skin texture, including texture discontinuities associated with skin aging. As used herein, prophylactically regulating such discontinuities includes delaying, minimizing and/or preventing visible and/or tactile discontinuities in the texture of mammalian skin, to thereby provide improved skin appearance and/or feel, e.g., a smoother, more even appearance and/or feel.

The composition of the present invention are also useful for promoting exfoliation or desquamation or turnover of the skin. Without intending to be bound or limited by theory, it is believed that the compositions containing the vitamin $B_3$ compound, particularly niacinamide, strengthen the energy state of cells regulating exfoliation, resulting in normalization of epidermal differentiation, keratinization, and turnover.

The compositions of the present invention are still further useful for moisturizing the skin. Without intending to be bound or limited by theory, it is believed that the compositions containing the vitamin $B_3$ compound, particularly niacinamide and/or tocopherol nicotinate, increase skin moisturization or hydration by several different mechanisms. One mechanism involves the effect of vitamin $B_3$ compounds on natural moisturizing factors. Natural moisturizing factors include the water-binding, metabolic by-products of skin proteins, especially filaggrin. It is believed that vitamin $B_3$ compounds increase the level of the above mentioned skin proteins, thereby increasing the level of natural moisturizing factors and, thus, moisturization. Another mechanism involves the effect of vitamin $B_3$ compounds on the level and/or molecular weight of keratin proteins in the stratum corneum. These proteins bind water and aid in providing flexibility to the corneum cell layer. Increased keratin level, thus, increases the concentration of moisture-binding proteins, resulting in improved skin moisturization. The degree of skin moisturization attained or stratum corneum flexibility achieved as a result of hydration is also related to the type of keratin present Mature stratum corneum cell layers contain keratin proteins of higher molecular weight than those found in the viable epidermal cell layers. These higher molecular weight keratins (e.g., keratins having a molecular weight of about 67,000) tend to bind more water and/or provide greater stratum corneum flexibility. It is believed that Vitamin $B_3$ compounds stimulate production of these higher molecular weight keratin. A third mechanism involves the effect of Vitamin $B_3$ compounds on the level of involucrin and desmosomal proteins. Involucrin is a protein precursor to the stratum corneum cell envelop which encases the keratin proteins and natural moisturizing factors. Desmosomal proteins are in close association with the stratum corneum cell envelop and aid in connecting the stratum corneum cells. Vitamin $B_3$ compounds increase the level of involucrin and desmosomal proteins. Increased involucrin and the desmosomal protein levels augment and strengthen the corneum cell envelope, helping to retard the dehydration of the encased keratins and natural moisturizing factors and, thereby, improving skin moisturization.

The compositions of the present invention, including the essential and optional components thereof, are described in detail hereinafter.

ESSENTIAL COMPONENTS

Vitamin $B_3$ Component

The compositions of the present invention comprise a safe and effective amount of a natural or synthetic vitamin $B_3$ compound. The compositions of the present invention preferably comprise from about 0.01% to about 50%, more preferably from about 0.01% to about 40%, even more preferably from about 1% to about 20%, and still more preferably from about 1% to about 10%, most preferably from about 1% to about 5%, of the vitamin $B_3$ compound.

As used herein, "vitamin $B_3$ compound" means a compound having the formula:

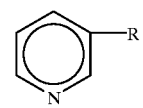

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Suitable esters of nicotinic acid include nicotinic acid esters of $C_1$–$C_{22}$, preferably $C_1$–$C_{16}$, more preferably $C_1$–$C_6$ alcohols. The alcohols are suitably straight-chain or branched chain, cyclic or acyclic, saturated or unsaturated (including aromatic), and substituted or unsubstituted. The esters are preferably non-rubifacient. As used herein, "non-rubifacient" means that the ester does not commonly yield a visible flushing response after application to the skin in the subject compositions (the majority of the general population would not experience a visible flushing response, although such compounds may cause vasodilation not visible to the naked eye). Alternatively, a nicotinic acid material which is rubifacient at higher doses could be used at a lower dose at which a rubifacient response does not occur. Non-rubifacient esters of nicotinic acid include, but are not limited to, tocopherol nicotinate and inositol hexanicotinate; tocopherol nicotinate is preferred.

Other derivatives of the vitamin $B_3$ compound are derivatives of niacinamide resulting from substitution of one or more of the amide group hydrogens. Nonlimiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1–C18). Specific examples of such derivatives include nicotinuric acid and nicotinyl hydroxamic acid, which have the following chemical structures:

nicotinuric acid:

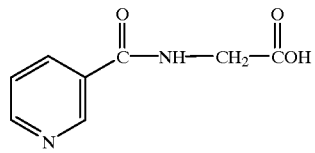

nicotinyl hydroxamic acid:

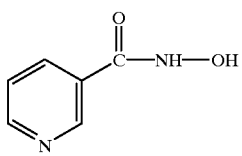

Exemplary nicotinyl alcohol esters include nicotinyl alcohol esters of the carboxylic acids salicylic acid, acetic acid, glycolic acid, palmitic acid and the like. Other non-limiting examples of vitamin $B_3$ compounds useful herein are 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl)urea, 2-mercaptonicotinic acid, nicomol, and niaprazine.

Examples of the above vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin $B_3$ compounds may be used herein. Preferred vitamin $B_3$ compounds are niacinamide and tocopherol nicotinate. Niacinamide is more preferred.

When used, salts, derivatives, and salt derivatives of niacinamide are preferably those having substantially the same efficacy as niacinamide in the methods of regulating skin condition described herein.

Salts of the vitamin $B_3$ compound are also useful herein. Nonlimiting examples of salts of the vitamin $B_3$ compound useful herein include organic or inorganic salts, such as inorganic salts with anionic inorganic species (e.g., chloride, bromide, iodide, carbonate, preferably chloride), and organic carboxylic acid salts (including mono-, di- and tri-$C_1$–$C_{18}$ carboxylic acid salts, e.g., acetate, salicylate, glycolate, lactate, malate, citrate, preferably monocarboxylic acid salts such as acetate). These and other salts of the vitamin $B_3$ compound can be readily prepared by the skilled artisan, for example, as described by W. Wenner, "The Reaction of L-Ascorbic and D-Isoascorbic Acid with Nicotinic Acid and Its Amide", J. Organic Chemistry, VOL. 14, 22–26 (1949), which is incorporated herein by reference. Wenner describes the synthesis of the ascorbic acid salt of niacinamide.

In a preferred embodiment, the ring nitrogen of the vitamin $B_3$ compound is substantially chemically free (e.g., unbound and/or unhindered), or after delivery to the skin becomes substantially chemically free ("chemically free" is hereinafter alternatively referred to as "uncomplexed"). More preferably, the vitamin $B_3$ compound is essentially uncomplexed. Therefore, if the composition contains the vitamin $B_3$ compound in a salt or otherwise complexed form, such complex is preferably substantially reversible, more preferably essentially reversible, upon delivery of the composition to the skin. For example, such complex should be substantially reversible at a pH of from about 5.0 to about 6.0. Such reversibility can be readily determined by one having ordinary skill in the art.

More preferably the vitamin $B_3$ compound is substantially uncomplexed in the composition prior to delivery to the skin. Exemplary approaches to minimizing or preventing the formation of undesirable complexes include omission of materials which form substantially irreversible or other complexes with the vitamin $B_3$ compound, pH adjustment, ionic strength adjustment, the use of surfactants, and formulating wherein the vitamin $B_3$ compound and materials which complex therewith are in different phases. Such approaches are well within the level of ordinary skill in the art.

Thus, in a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form. The vitamin $B_3$ compound in the compositions hereof having a pH of from about 4 to about 7 typically contain less than about 50% of the salt form.

The vitamin $B_3$ compound may be included as the substantially pure material, or as an extract obtained by suitable physical and/or chemical isolation from natural (e.g., plant) sources. The vitamin $B_3$ compound is preferably substantially pure, more preferably essentially pure.

Polycyclic compounds

Also essential to the compositions of the present invention is a polycyclic compound selected from the group consisting of select flavonoids, triterpenoids (also referred to as saponins), sterols, and mixtures thereof.

Flavonoids are broadly disclosed in U.S. Pat. Nos. 5,686,082 and 5,686,367, both of which are herein incorporated by reference. Flavonoids suitable for use in the present invention are flavanones selected from the group consisting of unsubstituted flavanones, mono-substituted flavanones, and mixtures thereof; chalcones selected from the group consisting of unsubstituted chalcones, mono-substituted chalcones, di-substituted chalcones, tri-substituted chalcones, and mixtures thereof; flavones selected from the group consisting of unsubstituted flavones, mono-substituted flavones, di-substituted flavones, and mixtures thereof; one or more isoflavones; coumarins selected from the group consisting of unsubstituted coumarins, mono-substituted coumarins, di-substituted coumarins, and mixtures thereof; chromones selected from the group consisting of unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1–C8 alkyl, C1–C4 alkoxyl, O-glycoside, or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof. Most preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., an ester or ether derivative prepared following extraction from a natural source).

Mixtures of the above flavonoid compounds may also be used.

The triterpenoids useful herein are also well known in the art and are described in U.S. Pat. Nos. 5,679,828; 5,643,884; 5,629,351; 5,529,769; and 5,064,823, all of which are herein incorporated by reference. Preferred triterpenoids include betulinic acid, boswellic acid, and mixtures thereof.

Sterols useful in the present invention are described in U.S. Pat. Nos. 5,665,366; 4,883,659; and 4,224,319, all of which are herein incorporated by reference. Preferred sterols include stigmastanol, stigmasterol, brassicasterol, campesterol, and mixtures thereof.

Mixtures of the above polycyclic compounds may also be used.

The herein described polycyclic compounds are preferably present in the instant invention at concentrations of from about 0.01% to about 20%, more preferably from about 0.1% to about 10%, and most preferably from about 0.1% to about 5%.

Polycyclic compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Carrier

Another essential ingredient of the present invention is a dermatologically acceptable carrier. The phrase "dermatologically-acceptable carrier", as used herein, means that the carrier is suitable for topical application to the skin, has good aesthetic properties, is compatible with the actives of the present invention and any other components, and will not cause any untoward safety or toxicity concerns. A safe and effective amount of carrier is from about 50% to about 99.99%, preferably from about 99.9% to about 80%, more preferably from about 98% to about 90%, most preferably from about 95% to about 90% of the composition.

The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g, from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like). Examples of topical carrier systems useful in the present invention are described in the following four references all of which are incorporated herein by reference in their entirety: "Sun Products Formulary" *Cosmetics & Toiletries,* vol. 105, pp. 122–139 (December 1990); "Sun Products Formulary", *Cosmetics & Toiletries,* vol. 102, pp. 117–136 (March 1987); U.S. Pat. No. 4,960,764 to Figueroa et al., issued Oct. 2, 1990; and U.S. Pat. No. 4,254,105 to Fukuda et al., issued Mar. 3, 1981.

The carriers of the present invention can comprise from about 50% to about 99% by weight of the compositions of the present invention, preferably from about 75% to about 99%, and most preferably from about 85% to about 95%.

Preferred cosmetically and/or pharmaceutically acceptable topical carriers include hydro-alcoholic systems and oil-in-water emulsions. When the carrier is a hydro-alcoholic system, the carrier can comprise from about 0% to about 99% of ethanol, isopropanol, or mixtures thereof, and from about 1% to about 99% of water. More preferred is a carrier comprising from about 5% to about 60% of ethanol, isopropanol, or mixtures thereof, and from about 40% to about 95% of water. Especially preferred is a carrier comprising from about 20% to about 50% of ethanol, isopropanol, or mixtures thereof, and from about 50% to about 80% of water. When the carrier is an oil-in-water emulsion, the carrier can include any of the common excipient ingredients for preparing these emulsions. A more detailed discussion of suitable carriers is found in U.S. Pat. No. 5,605,894 to Blank et al., and, U.S. Pat. No. 5,681,852 to Bissett, both of which are herein incorporated by reference in their entirety.

OPTIONAL COMPONENTS

The skin regulating compositions of the present invention may optionally comprise additional skin actives. Non-limiting examples of such skin actives include hydroxy acids such as salicylic acid; exfoliation or desquamatory agents such as zwitterionic surfactants; sunscreens such as 2-ethylhexyl-p-methoxycinnamate, 4,4'-t-butyl methoxydibenzoyl-methane, octocrylene, phenyl benzimidazole sulfonic acid; sun-blocks such as zinc oxide and titanium dioxide; anti-inflammatory agents; anti-oxidants/radical scavengers such as tocopherol and esters thereof; metal chelators, especially iron chelators; retinoids such as retinol, retinyl palmitate, retinyl acetate, retinyl propionate, and retinal; N-acetyl-L-cysteine and derivatives thereof; hydroxy acids such as glycolic acid; keto acids such as pyruvic acid; benzofuran derivatives; depilatory agents (e.g., sulfhydryl compounds); skin lightening agents (e.g., arbutin, kojic acid, hydroquinone, ascorbic acid and derivatives such as ascorbyl phosphate salts, placental extract, and the like); anti-cellulite agents (e.g., caffeine, theophylline); moisturizing agents; anti-microbial agents; anti-androgens; and skin protectants. Mixtures of any of the above mentioned skin actives may also be used. A more detailed description of these actives is found in U.S. Pat. No. 5,605,894 to Blank et al. (previously incorporated by reference). Preferred skin actives include hydroxy acids such as salicylic acid, sunscreen, antioxidants and mixtures thereof.

Other conventional skin care product additives may also be included in the compositions of the present invention. For example, urea, guanidine, glycerol, petrolatum, mineral oil, sugar esters and polyesters, polyolefins, methyl isostearate, ethyl isostearate, cetyl ricinoleate, isononyl isononanoate, isohexadecane, lanolin, lanolin esters, cholesterol, pyrrolidone carboxylic acid/salt (PCA), trimethyl glycine (betaine), tranexamic acid, amino acids (e.g., serine, alanine, threonine, histidine) and/or their salts, panthenol and its derivatives, collagen, hyaluronic acid, elastin, hydrolysates, primrose oil, jojoba oil, epidermal growth factor, soybean saponins, mucopolysaccharides, and mixtures thereof may be used. Other suitable additives or skin actives are discussed in further detail in PCT application WO 97/39733, published Oct. 30, 1997, to Oblong et al., herein incorporated by reference in its entirety.

Preparation of Compositions

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like.

Methods for Regulating Skin Condition

The compositions of the present invention are useful for regulating mammalian skin condition (especially human skin, more especially human facial skin), including visible and/or tactile discontinuities in skin, signs of skin aging, and visible and/or tactile discontinuities in skin associated with skin aging (including fine lines, wrinkles, large pores, surface roughness, dryness and other texture discontinuities associated with aged skin). Such regulation includes prophylactic and therapeutic regulation.

Regulating skin condition involves topically applying to the skin a safe and effective amount of a composition of the present invention. The amount of the composition which is applied, the frequency of application and the period of use will vary widely depending upon the level of vitamin $B_3$ compound and/or other components of a given composition and the level of regulation desired, e.g., in light of the level of skin aging present in the subject and the rate of further skin aging.

In a preferred embodiment, the composition is chronically applied to the skin. By "chronic topical application" is meant continued topical application of the composition over an extended period during the subject's lifetime, preferably for a period of at least about one week, more preferably for a period of at least one month, even more preferably for at least about three months, even more preferably for at least about six months, and more preferably still for at least about one year. While benefits are obtainable after various maximum periods of use (e.g., five, ten or twenty years), it is preferred that chronic application continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions which are typically applied per application are, in mg composition/cm² skin, from about 0.1 mg/cm² to about 10 mg/cm². A particularly useful application amount is about 2 mg/cm².

Regulating skin condition is preferably practiced by applying a composition in the form of a skin lotion, cream, gel, emulsion, spray, conditioner, cosmetic, lipstick, foundation, nail polish, or the like which is intended to be left on the skin for some esthetic, prophylactic, therapeutic or other benefit (i.e., a "leave-on" composition). After applying the composition to the skin, it is preferably left on the skin for a period of at least about 15 minutes, more preferably at least about 30 minutes, even more preferably at least about 1 hour, most preferably for at least several hours, e.g., up to about 12 hours. Any part of the external portion of the face, hair, and/or nails can be treated, e.g., face, lips, under-eye area, eyelids, scalp, neck, torso, arms, hands, legs, fingernails, toenails, scalp hair, eyelashes, eyebrows, etc.

Another approach to ensure a continuous exposure of the skin to at least a minimum level of vitamin $B_3$ compound is to apply the compound by use of a patch applied, e.g. to the face. Such an approach is particularly useful for problem skin areas needing more intensive treatment. The patch can be occlusive, semi-occlusive or non-occlusive. The vitamin $B_3$ compound composition can be contained within the patch or be applied to the skin prior to application of the patch. The patch can also include additional actives such as chemical initiators for exothermic reactions such as those described in PCT application WO 9701313 to Burkett et al. The patch is preferably left on the skin for a period of at least about 15 minutes, more preferably at least about 30 minutes, even more preferably at least about 1 hour, most preferably at night as a form of night therapy.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

A skin cream is prepared by conventional methods from the following components.

| | Ingredient (CTFA Name) | Weight % |
|---|---|---|
| PHASE A: | Water U.S.P. | 55.31 |
| | Disodium EDTA | 0.13 |
| | Methyl Paraben | 0.25 |
| | Glycerin | 3.00 |
| | 2',4-dihydroxy chalcone | 2.00 |
| | Zinc Citrate | 1.00 |
| PHASE B: | Cetyl Alcohol | 0.56 |
| | Stearyl Alcohol | 2.03 |
| | Behenyl Alcohol | 0.22 |
| | Steareth-21 (Brij 721) | 0.37 |
| | Steareth-2 (Brij 72) | 1.10 |
| | Distearyldimonium chloride Varisoft TA-100) | 0.95 |
| | Propyl Paraben | 0.10 |
| | Polypropylene glycol-15 stearyl ether (Arlamol E) | 3.25 |
| PHASE C: | Polypropylene glycol-15 stearyl ether) (Arlamol E) | 2.17 |
| | titanium dioxide | 0.75 |
| PHASE D: | Niacinamide | 5.00 |
| | Citric acid | 0.19 |
| | water U.S.P. | 17.00 |
| | 50% NaOH | 0.94 |
| PHASE E: | Benzyl Alcohol | 0.50 |
| | Silicone fluid (DC Q2 - 1401; cyclomethicone/dimethiconol - 50/50 blend | 0.75 |
| | dimethicone 10 cst | 1.00 |
| | polyethylene Low Density Beads | 1.00 |

-continued

A skin cream is prepared by conventional methods from the following components.

| Ingredient (CTFA Name) | Weight % |
| --- | --- |
| PHASE F: Fragrance | 0.10 |
| PHASE G: 50% NaOH | 0.33 |

Blend the A phase components with a suitable mixer (e.g., Tekmar model RW20DZM), heating while stirring to a temperature of 70–80° C. Separately, blend the B phase components with a suitable mixer and heat with mixing to melt the components. Separately, blend the C phase components and mill to obtain an acceptably smooth mixture (e.g., using a Tekmar T50 Mill).

Add the C phase mixture to the B phase mixture and mix. Then add the resulting mix to the A phase mixture with mixing, cool with a cold water bath and mill, then continue stirring. Remove the combination from the bath, with continued stirring, once the temperature reaches 40° C.

Separately, blend the D phase components by stirring until dissolved, then add this to the combination of A–C materials.

Separately, blend the E phase components by mixing until smooth and continuous, then add this to the combination of the A–D materials. Add and mix the fragrance, then the NaOH. Adjust the pH as necessary to 5.5.

Apply the composition to a subject's wrinkled, aged, or photodamaged facial skin at the rate of 2 mg composition cm$^2$ skin once or twice daily for a period of at least 3–6 months to reduce fine lines and wrinkles and improve skin surface texture.

Alternatively, the 2',4-dihydroxy chalcone can be replaced with an equivalent quantity of another polycyclic compound (e.g., another chalcone, flavanone, isoflavone, coumarin, flavone, chromone, dicoumarol, chromanone, chromanol, triterpenoid (e.g., betulinic acid), sterol (e.g., stigmasterol), or mixtures thereof).

Example 2

An emulsion is prepared by conventional methods from the following components:

| Ingredient | Weight % |
| --- | --- |
| Silicone fluid (Dow Corning DC 345) | 15.0 |
| Silicone fluid (Dow Corning DC 3225C) | 2.5 |
| Silicone fluid (Goldschmidt Abil We09) | 2.5 |
| Water | 66.4 |
| Niacinamide | 5.0 |
| Uusubstituted flavanone | 5.0 |
| Tetrasodium EDTA | 0.1 |
| Benzyl alcohol | 0.3 |
| Methyl paraben | 0.2 |
| Glycerin | 3.0 |

Form the water phase in a suitable vessel charged with the water as follows: add the glycerin and then niacinamide to the water with stirring. Add to this mixture with stirring the methyl paraben dissolved in the benzyl alcohol. Add to this mixture with stirring the EDTA.

Form the silicone phase in a separate suitable vessel by adding and stirring together the silicone fluids and the unsubstituted flavanone.

Add the water phase to the silicone phase slowly with stirring to form the emulsion.

Apply the resulting composition to a subject's wrinkled, aged, or photodamaged facial skin at the rate of 2 mg composition/cm$^2$ skin once or twice daily for a period of at least 3–6 months to reduce fine lines and wrinkles and improve skin surface texture.

Alternatively, the unsubstituted flavanone can be replaced with an equivalent quantity of another polycyclic compound (e.g., chalcone, another flavanone, isoflavone, coumarin, flavone, chromone, dicoumarol, chromanone, chromanol, triterpenoid (e.g., betulinic acid), sterol (e.g., stigmasterol), or mixtures thereof).

Example 3

A skin cream is prepared by conventional methods from the following components.

| | Ingredient (CTFA Name) | Weight % |
| --- | --- | --- |
| PHASE A: | Water U.S.P | 63.46 |
| | Disodium EDTA | 0.15 |
| | Glycerin | 5 |
| | Boswellic acid | 0.5 |
| PHASE B: | Cetyl hydroxy ethyl cellulose | 0.15 |
| | Methyl Paraben | 0.25 |
| PHASE C: | Cetyl Alcohol | 0.5 |
| | Stearyl Alcohol | 0.5 |
| | Behenyl Alcohol | 0.5 |
| | Cetyl ricinoleate | 3 |
| | Steareth-2 (Brij 72) | 1.05 |
| | Distearyldimonium chloride (Varisoft TA-100) | 0.25 |
| | Propyl Paraben | 0.10 |
| | Myristyl myristate | 1.5 |
| | Caprylic/Capritryglycerides | 1.5 |
| | Mineral oil | 2 |
| | Fatty acid ester of sugar* | 1 |
| | Polypropylene glycol-15 stearyl ether (Arlamol E) | 1.05 |
| PHASE D: | dimethicone 10 cst (Dow Corning) | 2 |
| PHASE E: | Niacinamide | 5 |
| | Water U.S.P. | 10 |
| PHASE F: | Benzyl Alcohol | 0.5 |
| PHASE G: | 50% NaOH | 0.04 |

*A C1–C30 monoester or polyester of sugars and one or more carboxylic acid moieties as described herein, preferably a sucrose polyester in which the degree of esterification is 7–8, and in which the fatty acid moieties are C18 mono- and/or di-unsaturated and behenic acids, in a molar ratio of unsaturates: behenic acid of 1:7 to 3:5, more preferably the octaester of sucrose in which there are about 7 behenic fatty acid moieties and about 1 oleic acid moiety in the molecule, e.g., sucrose ester of cottonseed oil fatty acids.

Blend the A phase components with a suitable mixer (e.g., Tekmar model RW20DZM), heating while stirring to a temperature of about 70–80° C. Add the cetyl hyroxy ethyl cellulose and methyl paraben with mixing at about 70–80° C. to melt the components. Separately, blend the C phase components and mill to obtain an acceptably smooth mixture (e.g., using a Tekmar T50 Mill).

Add the C phase mixture to the above mixture and mix. Remove the combination from the bath, with continued stirring, once the temperature reaches about 45° C. Add the dimethicone and mix.

Separately, blend the E phase components by mixing until smooth and continuous, then add this to the above mixture. Add and mix in the benzyl alcohol, then the NaOH. Adjust the pH as necessary to 7.

Apply the composition to a subject's wrinkled, aged, or photodamaged facial skin at the rate of 2 mg composition/ cm² skin once or twice daily for a period of at least 3–6 months to reduce fine lines and wrinkles and improve skin surface texture.

Alternatively, the boswellic acid can be replaced with an equivalent quantity of another polycyclic compound (e.g., chalcone, flavanone, isoflavone, coumarin, flavone, chromone, dicoumarol, chromanone, chromanol, another triterpenoid (e.g., betulinic acid), sterol (e.g., stigmasterol), or mixtures thereof).

Example 4

A skin cream is prepared by conventional methods from the following components.

| | Component | Weight % |
|---|---|---|
| PHASE A: | benzyl alcohol | 0.30 |
| | methyl p-hydroxybenzoate (a.k.a. methylparaben) | 0.20 |
| | ethanol | 3.00 |
| PHASE B: | water | 59.60–60.35 |
| | disodium EDTA | 0.50 |
| | glycerol | 10.00 |
| | hexylene glycol | 2.00 |
| | niacinamide | 2.00 |
| | triethanol amine | 0.05 |
| | butylated hydroxytoluene | 0.10 |
| PHASE C: | Dow Corning 345 Fluid | 12.50 |
| | Abil WE-09 | 2.50 |
| | Dow Corning -3225C | 2.50 |
| | petrolatum | 1.50 |
| | stigmastanol | 1.00 |
| | retinol (10% in soybean oil) | 0.75–1.50 |
| | fatty acid ester of sugar* | 1.00 |

*See Example 3

Blend the A phase components with a suitable mixer (e.g., Tekmar model RW20DZM). Blend the B phase components into the A phase with a suitable mixer. Separately, blend the C phase components until they are uniform. Add the C phase mixture to the A/B phase mixture, mix until uniform and emulsified, and then mill to obtain an acceptably smooth mixture (e.g., using a Tekmar T50 Mill).

Apply the composition to a subject's wrinkled, intrinsically aged, or photodamaged facial skin at the rate of 2 mg composition/cm² skin once or twice daily for a period of at least 3–6 months to improve skin surface texture, including diminishing fine lines and wrinkles.

An alternative skin cream having reduced retinol levels can be prepared in the same manner from the above components wherein the retinol is added in an amount of 0.025% (0.25% of 10% retinol in soybean oil), quo sine to 100% with water, the amounts of the other components being as shown.

Alternatively, the stigmastanol can be replaced with an equivalent quantity of another polycyclic compound (e.g., chalcone, flavanone, isoflavone, coumarin, flavone, chromone, dicoumarol, chromanone, chromanol, triterpenoid (e.g., betulinic acid), another sterol (e.g., stigmasterol), or mixtures thereof).

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A topical composition comprising:
   (a) from about 0.01% to about 50% of a vitamin B3 compound;
   (b) from about 0.01% to about 20% of a polycyclic compound selected from the group consisting of:
      (i) flavanones selected from the group consisting of unsubstituted flavanones, mono-substituted flavanones, and mixtures thereof;
      (ii) chalcones selected from the group consisting of unsubstituted chalcones, mono-substituted chalcones, di-substituted chalcones, tri-substituted chalcones, and mixtures thereof;
      (iii) flavones selected from the group consisting of unsubstituted flavones, mono-substituted flavones, di-substituted flavones, and mixtures thereof;
      (iv) one or more isoflavones;
      (v) coumarins selected form the group consisting of unsubstituted coumarins, mono-substituted coumarins, di-substituted coumarins, and mixtures thereof;
      (vi) chromones selected from the group consisting of unsubstituted chromones, mono-substituted chromones, di-substituted chromones, and mixtures thereof;
      (vii) one or more dicoumarols;
      (viii) one or more chromanones;
      (ix) one or more chromanols; and
      (x) sterols selected from the group consisting of stigmasterol, stigmastanol, brassicasterol, campesterol, and mixtures thereof;
      (xi) triterpenoids selected from the group consisting of betulinic acid, boswellic acid, and mixtures thereof; and
      (x) mixtures thereof;
   and
   (c) a dermatologically acceptable carrier for the vitamin B3 compound and the polycyclic compound.

2. A composition according to claim 1, wherein said vitamin $B_3$ compound is selected from niacinamide, derivatives of niacinamide, non-vasodilating esters of nicotinic acid, and mixtures thereof.

3. A composition according to claim 2, wherein said vitamin $B_3$ compound is selected from niacinamide, tocopherol nicotinate, and mixtures thereof.

4. A composition according to claim 3, wherein said vitamin $B_3$ compound is niacinamide.

5. A composition according to claim 1 wherein the polycyclic compound selected from the group consisting of flavanones, chalcones, or mixtures thereof.

6. A composition according to claim 5 wherein the polycyclic compound is selected from the group consisting of unsubstituted flavanone, unsubstituted chalcone, or a mixture thereof.

7. A composition according to claim 1, wherein the composition further comprises an additional skin active selected from the group consisting of hydroxy acids, desquamatory agents, sunscreens, anti-oxidants, retinoids, moisturizing agents, and mixtures thereof.

8. A composition according to claim 7, wherein the hydroxy acid is salicylic acid; the desquamatory agent is selected from the group consisting of zwitterionic surfactants and mixtures thereof; the sunblock is selected from the group consisting of zinc oxide, titanium dioxide and mixtures thereof; the sunscreen is selected from the group consisting of 2-ethylhexyl-p-methoxycinnamate, 4,4'-t-butyl methoxydibenzoyl-methane, phenyl benzimidazole sulfonic acid, octocrylene and mixtures thereof; the anti-oxidant is selected from the group consisting of tocopherol, esters thereof and mixtures thereof; the moisturizing agent is selected from the group consisting of glycerol, urea, guanidine, petrolatum, panthenol, fatty acids esters of polyols and sugars, and mixtures thereof; and the retinoid is selected from the group consisting of retinol, retinyl acetate, retinyl propionate, and mixtures thereof.

9. A method of treating or preventing skin conditions, comprising applying to the skin of a mammal a safe and effective amount of the composition of claim 1.

10. A method of regulating skin condition, comprising applying to the skin of a mammal a safe and effective amount of a composition of claim 1.

* * * * *